(12) United States Patent
Hansegard et al.

(10) Patent No.: US 9,107,607 B2
(45) Date of Patent: Aug. 18, 2015

(54) METHOD AND SYSTEM FOR MEASURING DIMENSIONS IN VOLUMETRIC ULTRASOUND DATA

(75) Inventors: Joger Hansegard, Oslo (NO); Olivier Gerard, Oslo (NO)

(73) Assignee: General Electric Company, Schenectady, NY (US)

( * ) Notice: Subject to any disclaimer, the term of this patent is extended or adjusted under 35 U.S.C. 154(b) by 448 days.

(21) Appl. No.: 12/986,464

(22) Filed: Jan. 7, 2011

(65) Prior Publication Data

US 2012/0176365 A1 Jul. 12, 2012

(51) Int. Cl.
*G06T 17/00* (2006.01)
*A61B 8/08* (2006.01)
*G06T 15/08* (2011.01)
*A61B 8/00* (2006.01)
*A61B 5/107* (2006.01)

(52) U.S. Cl.
CPC .............. *A61B 8/085* (2013.01); *A61B 5/1077* (2013.01); *A61B 8/0858* (2013.01); *A61B 8/463* (2013.01); *A61B 8/466* (2013.01); *A61B 8/469* (2013.01); *A61B 8/483* (2013.01); *A61B 8/523* (2013.01); *G06T 15/08* (2013.01)

(58) Field of Classification Search
CPC ...................................................... G06T 15/08
USPC ......................................................... 345/424
See application file for complete search history.

(56) References Cited

U.S. PATENT DOCUMENTS

| 6,602,194 | B2 | 8/2003 | Roundhill et al. |
| 2006/0098853 | A1 | 5/2006 | Roundhill et al. |
| 2007/0249935 | A1 | 10/2007 | Deschinger et al. |
| 2007/0255136 | A1 | 11/2007 | Kristofferson et al. |
| 2007/0255137 | A1 | 11/2007 | Sui et al. |
| 2007/0255139 | A1 | 11/2007 | Deschinger et al. |
| 2010/0123715 | A1 | 5/2010 | Hansegard et al. |

FOREIGN PATENT DOCUMENTS

| CN | 101057787 A | 10/2007 |
| CN | 101061962 A | 10/2007 |
| WO | 2010018513 A2 | 2/2010 |

OTHER PUBLICATIONS

Liu, L., Bajaj, C., Deasy, J. O., Low, D. A. and Ju, T. (2008), Surface Reconstruction From Non-parallel Curve Networks. Computer Graphics Forum, 27: 155-163.*

(Continued)

*Primary Examiner* — Stephen R Koziol
*Assistant Examiner* — Robert Craddock
(74) *Attorney, Agent, or Firm* — Dean D. Small; The Small Patent Law Group, LLC

(57) ABSTRACT

A system for measuring distances includes a display for displaying a three-dimensional (3D) ultrasound dataset, a user interface for translating a slice plane through the 3D ultrasound dataset to define a first image plane at a first location and a second image plane at a second different location, and a processor for automatically determining a distance between the first and second image planes. A method of measuring distances and a non-transitory computer readable medium are also described herein.

20 Claims, 5 Drawing Sheets

(56) References Cited

OTHER PUBLICATIONS

R.J. Frank, H. Damasio, T.J. Grabowski, Brainvox: An Interactive, Multimodal Visualization and Analysis System for Neuroanatomical Imaging, NeuroImage, 5 (1997), pp. 13-30.*

Unofficial English Translation of Chinese Office Action and Search Report issued in connection with corresponding CN Application No. 201210042743.6 on Aug. 1, 2014.

* cited by examiner

METHOD AND SYSTEM FOR MEASURING DIMENSIONS IN VOLUMETRIC ULTRASOUND DATA

BACKGROUND OF THE INVENTION

The subject matter disclosed herein relates generally to diagnostic ultrasound systems, and more particularly, to a method and system for measuring dimensions in volumetric ultrasound data.

Physicians often rely on medical images to diagnose and assess a patient's medical condition. When assessing the medical condition it is often desirable to measure a distance between two different features. For example, during aortic valve replacement, it is important to measure the distance between the aortic valve plane and the onset of the coronary blood vessels. At least one conventional ultrasound system utilizes a virtual caliper to measure the distance between the aortic valve and the onset of a coronary artery. More specifically, the operator acquires a single two-dimensional (2D) image, also referred to herein as a slice plane, that includes both the aortic valve and the onset of a coronary artery. The operator then utilizes the conventional virtual caliper to measure the distance between the aorta and the left coronary on the 2D image.

This conventional measurement process relies upon the capability to position the ultrasound probe such that the 2 structures of interest are visible simultaneously in one single plane. This may prove to be difficult or even impossible. Another method is to use one volumetric acquisition and to reconstruct a single plane. However, it is often difficult to orient a single reconstructed slice plane such that the slice plane has sufficient visibility of the two features to enable the operator to properly mark and perform the distance measurement.

BRIEF DESCRIPTION OF THE INVENTION

In one embodiment, a method for measuring dimensions in volumetric ultrasound data is provided. The method includes positioning, in real-time a slice plane through the volumetric ultrasound dataset at a first location, receiving an operator input to begin a measurement, repositioning the slice plane to a different second location, and displaying a distance between the slice plane at the first and second locations on a display.

In another embodiment, a system for measuring dimensions in volumetric ultrasound data is provided. The system includes a display for displaying an volumetric ultrasound dataset, a user interface enabling an operator to position, in real-time a slice plane through the volumetric ultrasound dataset at a first location, receive an operator input to begin a measurement, and reposition the slice plane to a different second location, a processor computing a distance between the slice plane at the first and second locations, and a display displaying the computed distance.

In a further embodiment, a non-transitory computer readable medium for measuring dimensions in volumetric ultrasound data is provided. The non-transitory computer readable medium is programmed to receive an operator input to position, in real-time a slice plane through the volumetric ultrasound dataset at a first location, receive an operator input to begin a measurement, receive another operator input to reposition the slice plane to a different second location, and display a distance between the slice plane at the first and second locations on a display.

DETAILED DESCRIPTION OF THE INVENTION

Figure 1:
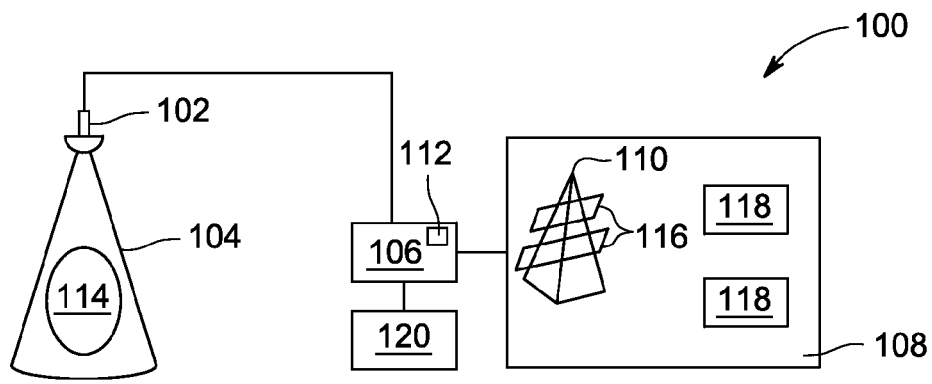
FIG. 1 illustrates a simplified block diagram of an ultrasound system formed in accordance with various embodiments.

The foregoing summary, as well as the following detailed description of certain embodiments of the present invention, will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

FIG. 1 illustrates a block diagram of an exemplary ultrasound system 100 that is formed in accordance with various embodiments. The ultrasound system 100 includes a an ultrasound probe 102 that is used to scan a region of interest (ROI) 104. A signal processor 106 processes the acquired ultrasound information received from the ultrasound probe and prepare frames of ultrasound information for display on a display 108. The acquired ultrasound information, referred to herein as a 3D volume dataset 110, is displayed on the display 108. The imaging system 100 also includes a measurement module 112 that enables an operator to measure the ROI 104, or an object 114, within the ROI 104. The measurement module 112 enables an operator to reposition or translate one or more slice planes 116 through the ROI 104 to identify a starting measurement position and an ending measurement position. The operator may view the position of the one or more slice planes 116 by view one or more 2D images 118 that are displayed on the display 108. The measurement module 112 then automatically determines a distance between the slice planes. The imaging system 100 also includes a user interface 120 that allows an operator to enter data, enter and change scanning parameters, access protocols, measure structures of interest, and the like. The user interface 120 also enable the operator to transmit and receive information to and from the measurement module 112, that instructs the measurement module 112 to reposition or translate one or more slice planes 116 through the ROI 104

Figure 2:
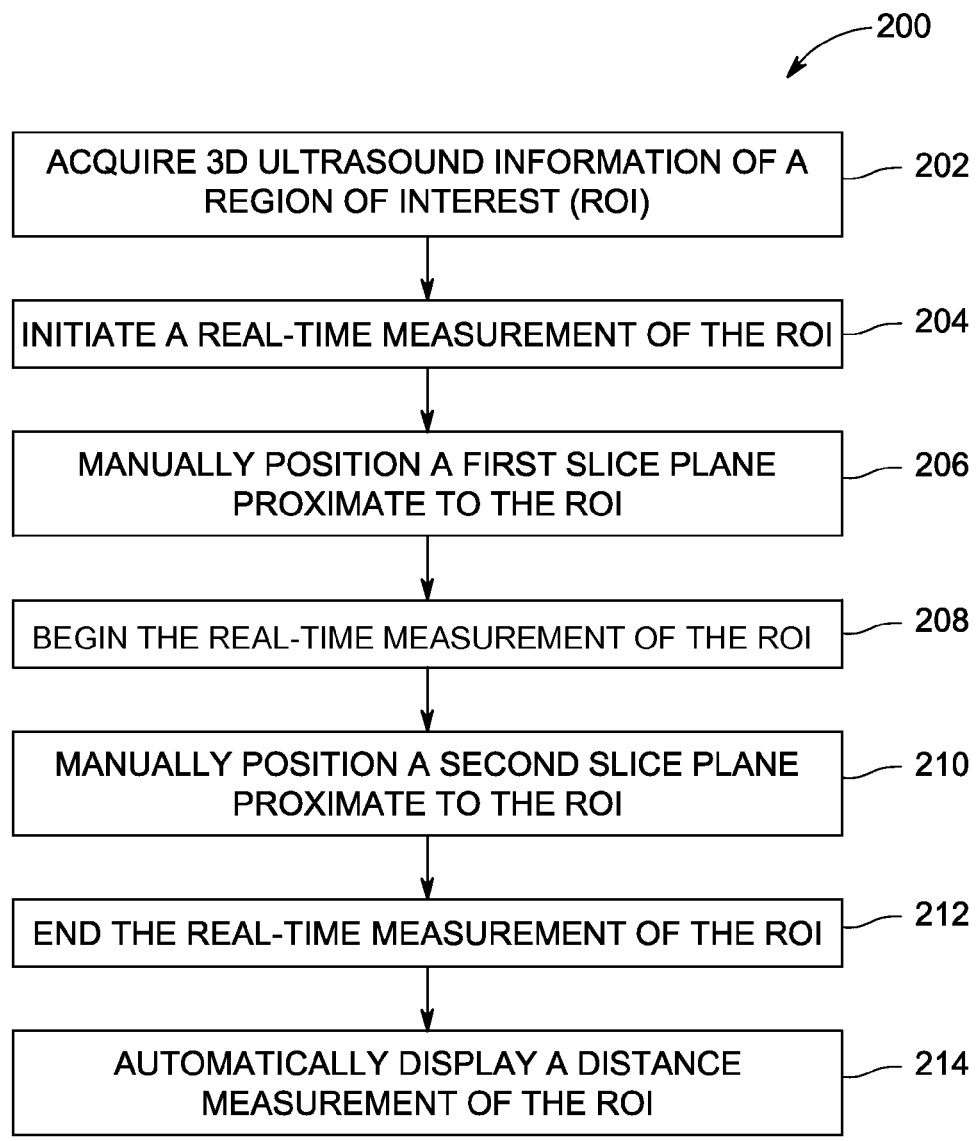
FIG. 2 is a flowchart of an exemplary method for locating and measuring a region of interest.
Figure 3:
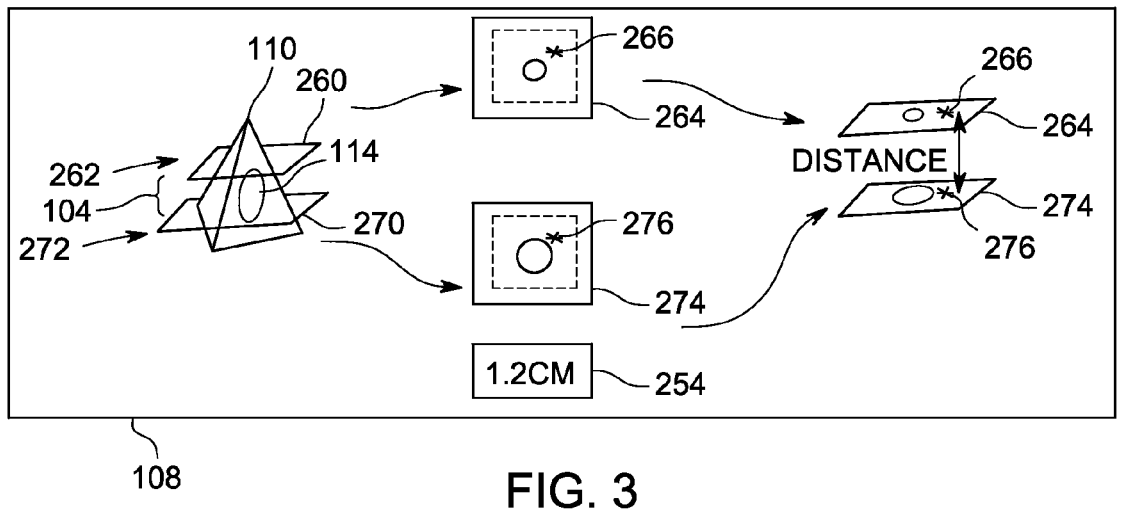
FIG. 3 illustrates an example of measuring a structure in accordance with various embodiments.

FIG. 2 is a flowchart illustrating an exemplary method 200 for locating and measuring a region of interest (ROI) within a three-dimensional (3D) volume dataset. FIG. 3 illustrates an example of measuring a ROI in accordance with the embodiment described in FIG. 2. The method 200 may be embodied as a set of instructions stored on the measurement module 112 shown in FIG. 1. The ROI may represent an object of interest, such as, for example, an aorta, a left coronary artery, etc. Optionally, the ROI may represent a distance between two objects of interest, such as for example, the aorta and the left coronary artery. The method 200 therefore may be utilized to measure a length, width, diameter, thickness, etc. of a single structure or a distance between two different structures.

At 202, ultrasound information is acquired of a region of interest (ROI), such as for example ROI 104 (shown in FIGS. 1 and 3). In the exemplary embodiment, the ROI 104 is embodied as a structure, such as for example, object 114 shown in FIG. 2. However, it should be realized that the ROI 104 may also be embodied as a distance between two or more different structures. The ultrasound information may be a volume of data including 3D color Doppler data over time, such as over one or more heart cycles, and may be stored in a memory device. Optionally, ultrasound information which has been previously acquired and stored in the memory device may be accessed for processing. An exemplary 3D volume dataset 110 acquired and/or accessed in step 202 is illustrated in FIG. 3. In the exemplary embodiment, the 3D volume dataset 110 is displayed in real-time on the display 108 to enable the operator to perform the measurements that are discussed in more detail below.

At 204, the operator initiates a real-time measurement of the ROI 104. For example, the operator may manually depress a button (not shown) on the user interface 120. In response to the button being depressed, a measurement indication 254 is displayed on the display 118 as shown in FIG. 3. The displayed measurement indication 254 provides a visual representation of the distance measurement. The measurement indication 254 is also utilized to inform the operator that the imaging system 100 has been initialized in a measurement mode and is configured to measure the length of the structure 114 or the distance between two or more different structures. The measurement indication 254 also provides real-time measurement information of the structure 114 or the distance between the two structures being measured.

At 206, the operator manually positions a slice plane 260 to identify a 2D image or slice that includes at least a portion of the structure 114. As discussed above, the method 200 may be used to measure a length, width, diameter, thickness, etc. of a single structure or a distance between two different structures. Accordingly, at 206, the operator manually positions the slice plane 260 at a first location 262 to measure either the single structure 114 or a distance between two different structures (not shown). An exemplary 2D image 264 of the information located at the first location 262 is shown in FIG. 3. In the exemplary embodiment, the operator may configure the imaging system 100 to operate in a slice mode. In the slice mode, the operator may observe the movement of the slice plane 260, in real-time, via the 2D image 264, as the first slice plane 260 is being positioned or translated through the 3D volume dataset 110. It should be realized that the slice planes described herein may be overlayed on the 3D volume dataset 110 to enable an operator to observe both the position of the slice plane with respect to the 3D volume dataset 110. Additionally, a 2D image may be displayed concurrently with the 3D volume dataset 110 to enable the operator to visually observe the information within the 3D volume dataset 110 that is represented by the slice plane at its current position. Therefore, the slice planes described herein may be opaque representations overlayed on the visual representation 3D volume dataset 110. The slice planes may also be embodied as dashed lines forming a box, a colored box, etc.

In operation, the first slice plane 260 is positioned by the operator until the first slice plane 260 is at the first location 262 which represents a starting point at which the operator wishes to begin the measurement of either the structure 114 or a distance between two structures. For example, the starting point may represent the proximal end of the structure 114 being measured or a starting point to measure a distance between two different structures which the operator wishes to measure. In one embodiment, if the operator desires to measure a thickness of the structure 114, the operator positions the first slice plane 260 at the first location 262 which represents the proximal end of the structure 114 shown in the 2D image 264. The operator may reposition the slice planes described herein by viewing the movement of the slice plane(s) on the visual representation of the 3D volume dataset 110. To begin measurement, the operator may click on a point 266 in the first slice plane 260 or optionally click on a point in the 2D image 264. Optionally, the operator may click on a specific portion of the structure 114, in either the slice plane 260 or the 2D image 264 to begin the measurement.

At 208 the operator clicks on a point 266 in the first slice plane 260 to begin the measurement. Optionally, the operator may click on a specific portion of the structure 114 to begin the measurement. Additionally, once the operator has selected a point on the structure 114, the measurement indication 254 is zeroed out or set to zero as shown in FIG. 3.

At 210, the operator manually positions a different second slice plane 270 at a different second location 272. The second location 272 may identify a distal end of the structure 114. Optionally, the second location 272 may represent the location of a second different structure. An exemplary 2D image 274 of the second slice plane 270 at the second location 272 is shown in FIG. 3. Thus, the operator may use the reconstructed 2D images 264 and 274 to assist the operator in properly locating the first and second slice planes 260 and 270 at the first and second locations 262 and 272, respectively or to position and select the measurement starting and ending points. In operation the second slice plane 270 is positioned by the operator at a desired location at which the operator wishes to end the measurement of either the structure 114 or a distance between two structures. In this embodiment, the second slice plane 270 is moved along an axis and remains parallel to the first slice plane 260

It should be realized that in the exemplary embodiment, once the operator has set the position of the first slice plane 260, any further movement of the second slice plane 270 causes the measurement indication 254 to update. More specifically, once the first slice plane 260 is set at the first location 262, the measurement indication 254 continually updates as the second slice plane 270 is being positioned. The change in the measurement indication 254 represents the real-time distance between the first slice plane 260 at the first location 260 and the second slice plane 270 at its current location. Thus, as the second slice plane 270 is moved or translated through the 3D volume dataset 110, the measurement indication 254 automatically updates to provide a distance measurement between the first slice plane 260 and the second slice plane 270.

At 212, the operator enters a command, via the user interface 120, to end the measurement. To enter the end measurement command, the operator may click on any location in the second slice plane 270 when the slice plane 270 is at the second location 272 or click on the respective 2D image as discussed above. Optionally, the operator may click on a specific point 276 in the second slice plane 270 or the respective 2D image as discussed above.

At 214, the measurement indication 254 automatically provides a distance measurement that represents the distance between the first slice plane 260 and the second slice plane 270. In operation, the measurement indication 254 automatically provides a distance measurement between the selected point 266 on the first slice plane 260 and the selected point 276 on the second slice plane 270. It should be realized that in this embodiment, the first slice plane 260 is parallel to the second slice plane 270. Thus, the distance shown on the measurement indication 254 is derived by determining the Euclidian distance between the slice planes 260 and 270 or a distance between the points 266 and 276. In the exemplary embodiment, the distance may then be computed by converting the pixel positions into a metric coordinate system. The resulting distance is displayed on the display 118 as a measurement for the distance between the two structures or a length of a single structure.

Figure 4:
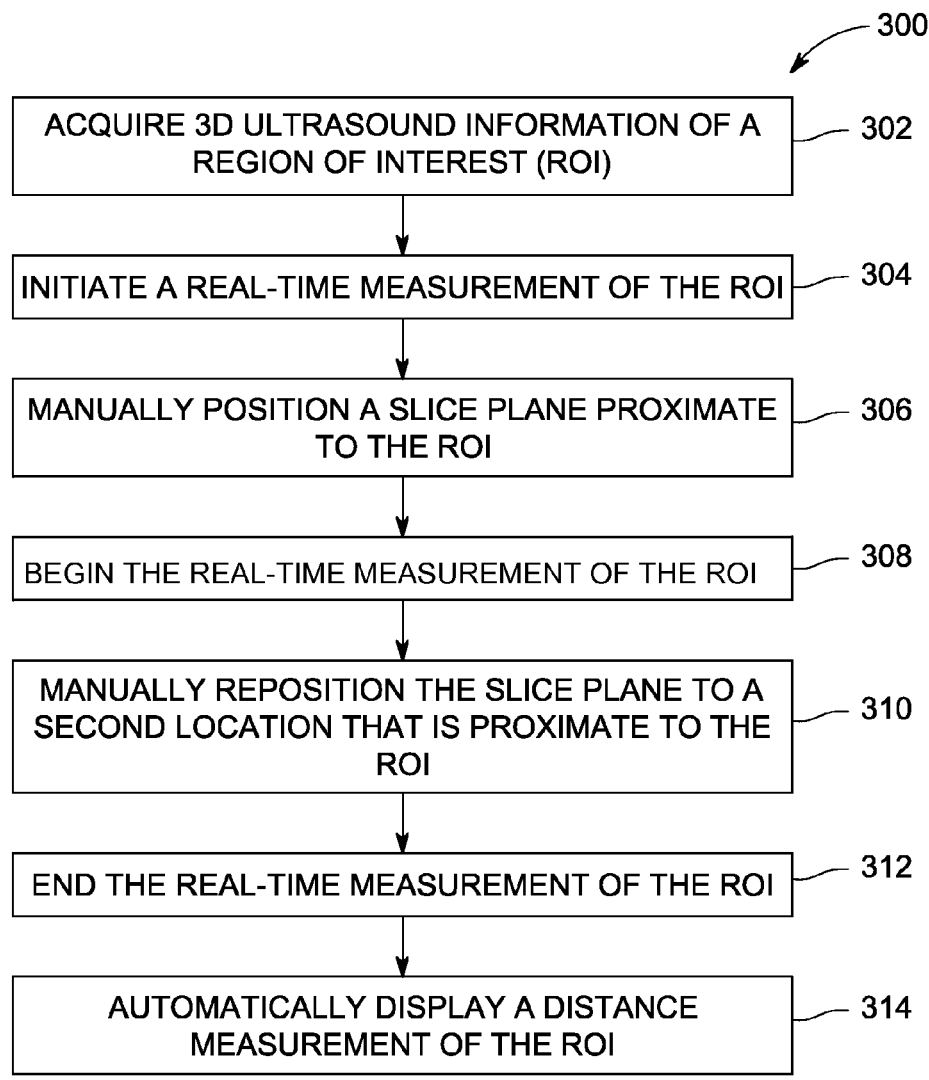
FIG. 4 is a flowchart of another exemplary method for locating and measuring a region of interest.
Figure 5:
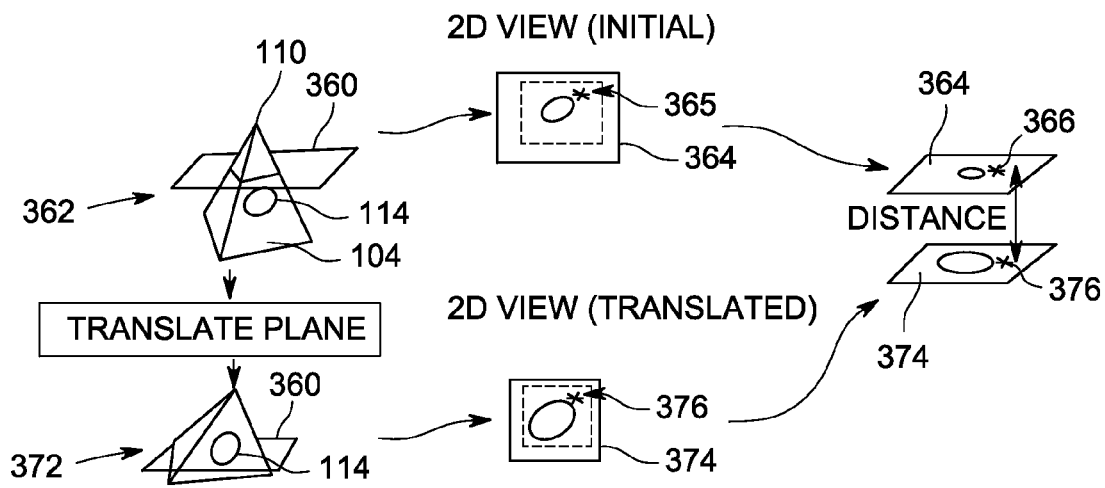
FIG. 5 illustrates another example of measuring a structure in accordance with various embodiments.

FIG. 4 illustrates another exemplary method 300 of measuring a ROI 104, such as structure 114, in accordance with various embodiments. FIG. 5 illustrates an example of measuring a ROI in accordance with the embodiment described in FIG. 4.

The method 300 is substantially similar to the method 200 described above. In this embodiment, the method 300 translates a single slice plane through the 3D volume dataset 110 to identify both the first and second ends of the structure 114 or a distance between two structures. The method 300 may therefore be utilized to measure a length, width, diameter, thickness, etc. of a single structure or a distance between two different structures.

At 302, ultrasound information is acquired of the ROI 104 similar to step 202 discussed above. In the exemplary embodiment, the ROI 104 is again embodied as the structure 114. However, it should be realized that the ROI 104 may be embodied as a distance between two different structures. At 304, the operator initiates a real-time measurement of either the structure 114 or a distance between two different structures (not shown) similar to step 204 discussed above.

At 306, the operator manually positions a slice plane 360 to identify a portion of the structure 114. As discussed above, the method 300 may be used to measure a length, width, diameter, thickness, etc. of a single structure or a distance between two different structures. Accordingly, at 306, the operator manually positions the slice plane 360 at a first location 362 to measure either the single structure 114 or a distance between two different structures (not shown). An exemplary 2D image 364 of the slice plane 360 of information at the first location 362 is shown in FIG. 4. In the exemplary embodiment, the operator may configure the imaging system 100 to operate in a slice mode. In the slice mode, the operator may observe the movement of the slice plane 360, in real-time, via the 2D image 364, as the slice plane 360 is being positioned or translated through the 3D volume dataset 110. In operation, the slice plane 360 is positioned by the operator until the slice plane 360 is at the first location 362 which represents a starting point in which the operator wishes to begin the measurement of either the structure 114 or a distance between two structures. Once the slice plane 360 is positioned at the first location 362, the operator clicks on the slice plane 360, via the user interface 120, to begin the measurement similar to step 208 discussed above. Accordingly, at 306, the operator may adjust the orientation of the slice plane 360 so that slice plane 360 is substantially perpendicular to the structure.

At 308 the measurement indication 254 is set to zero as shown in FIG. 4 and discussed above.

Figure 6:
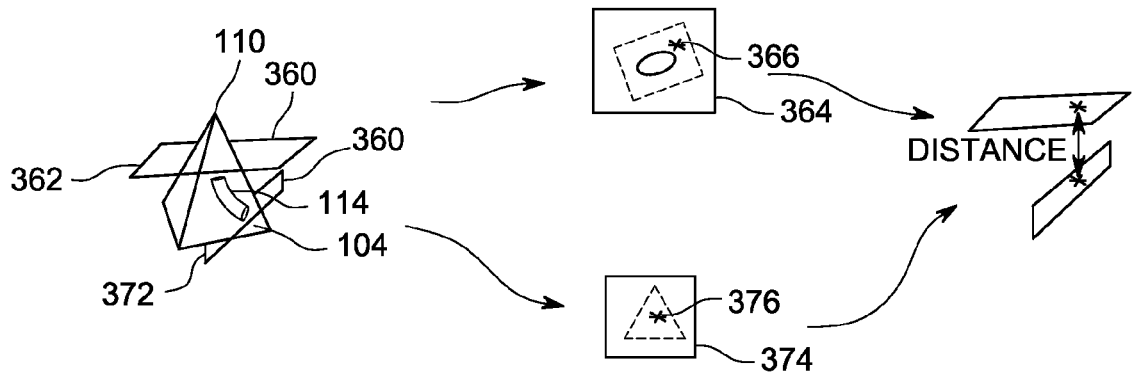
FIG. 6 illustrates another example of measuring a structure in accordance with various embodiments.

At 310, the operator manually moves or translates the slice plane 360 through the 3D volume dataset 110 until the slice plane 360 is at a different second location 372. The second location 372 may identify a distal end of the structure 114. Optionally, the second location 372 may represent the location of a second different structure. An exemplary 2D image 374 of the slice plane 370 at the second location 372 is shown in FIG. 4. Thus, the operator may use the reconstructed 2D images 364 and 374 to assist the operator in properly locating the slice plane 360 at the proximal and distal ends of the structure 114 or at the desired points on two different structures. It should be realized that in the exemplary embodiment, once the operator has entered the command at 306 to set the initial position of the slice plane 360, any further movement of the slice plane 360 causes the measurement indication 254 to update. More specifically, once the slice plane 360 is set at the first location 362 by entering the command at 306, the measurement indication 254 continually updates as the slice plane 360 is being translated through the 3D volume dataset. The change in the measurement indication 254 represents the real-time distance between the slice plane 360 at the first location 360 and the slice plane 360 at its current location. In the embodiment shown in FIG. 4, the slice plane 360 is translated along a parallel path between the first location 362 and the second location 372. In another embodiment, shown in FIG. 6, the slice plane 360 is translated along a non-parallel path between the first location 362 and the second location 372. The embodiment shown in FIG. 6 may be utilized to perform measurements on various structures that are curved or have some other shape that is preferably measured by translation, rotating, or otherwise positioning the slice plane 360 at various angles.

At 312, the operator enters a command, via the user interface 120, to end the measurement. To enter the end measurement command, the operator may click on any location in the slice plane 360 when the slice plane 360 is at the second location 372. Optionally, the operator may click on a specific point 376 in the slice plane 360.

At 314, the measurement indication 254 automatically provides a distance measurement that represents the distance between a point 365 in the first image 364 at the first location 362 and a point 376 in the second image 374 the second location 372. In operation, the measurement indication 254 automatically provides a distance measurement between the selected point 366 and the selected point 376. It should be realized that in this embodiment, the slice plane 360 at the first location 362 is parallel to the slice plane 360 at the second location 372. Thus, the distance shown on the measurement indication 254 is derived by determining the Euclidian distance between the slice plane 360 at the first and second locations 362 and 372 or a distance between the points 366 and 376. In the exemplary embodiment, the distance may then be computed by converting the pixel positions into a metric coordinate system. The resulting distance is displayed on the display 118 as a measurement for the distance between the two structures or a length of a single structure.

Figure 7:
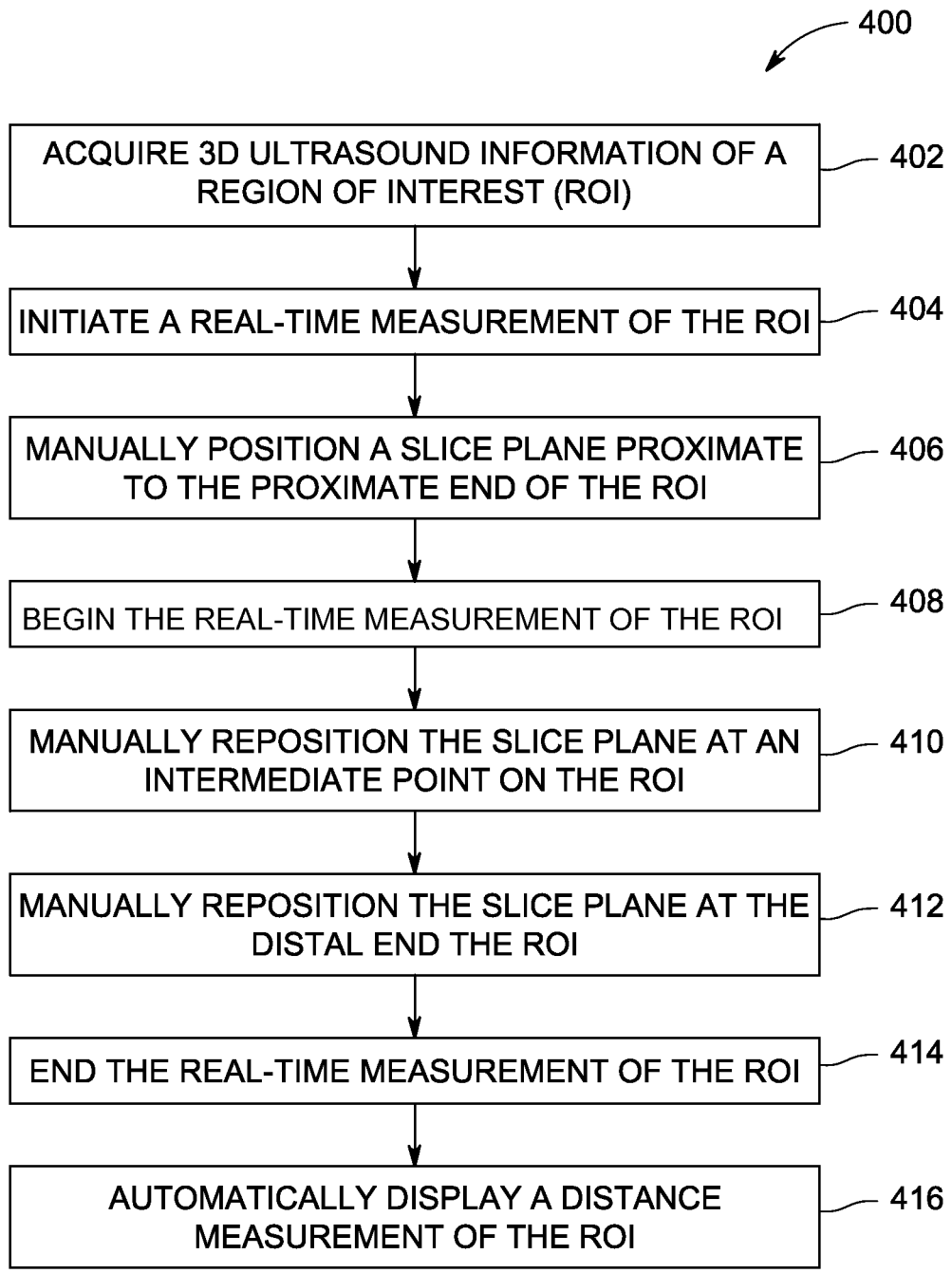
FIG. 7 is a flowchart of another exemplary method for locating and measuring a region of interest.
Figure 8:
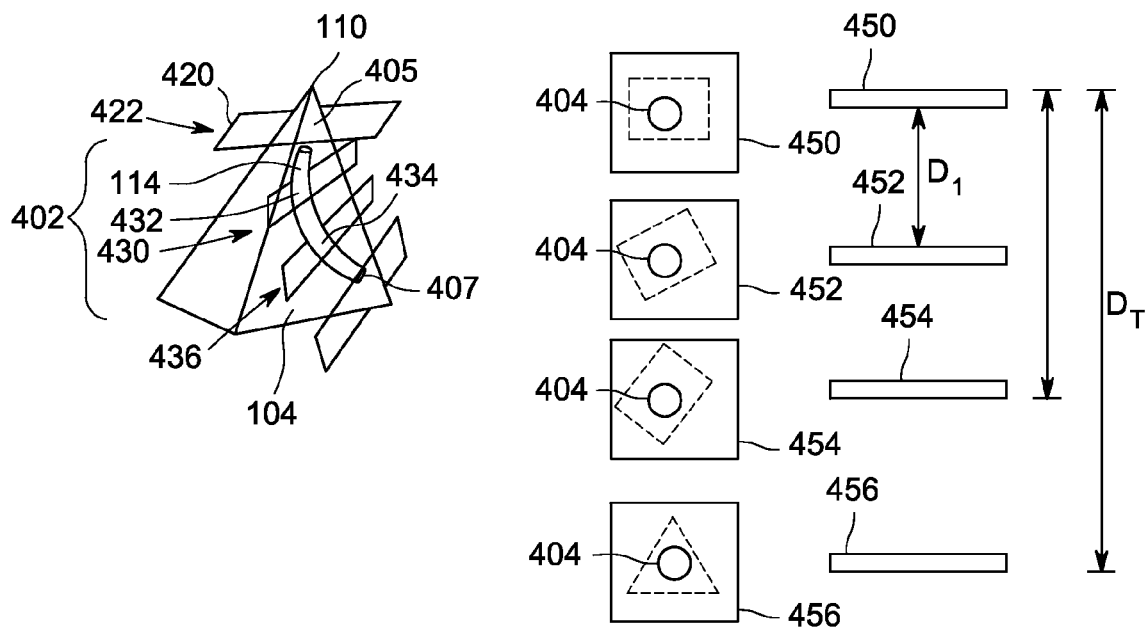
FIG. 8 illustrates another example of measuring a structure in accordance with various embodiments.

FIG. 7 is illustrates another exemplary method 400 of measuring a ROI 104, such as structure 114, in accordance with various embodiments. FIG. 8 illustrates an example of measuring the ROI 104 in accordance with the embodiment described in FIG. 7. In this embodiment, the method 400 translates a single slice plane through the 3D volume dataset 110 between a proximal end 405 and a distal end 407 of the structure 114 to measure the total distance or length of the structure 114 or a distance between two structures. The method 400 may therefore be utilized to measure a length, width, diameter, thickness, etc. of the non-linear structure 114 or a distance between two different structures.

At 404, ultrasound information is acquired of the ROI 104 similar to step 202 discussed above. In the exemplary embodiment, the ROI 104 is embodied as the structure 114. However, it should be realized that the ROI 104 may be embodied as a distance between two different structures. At 404, the operator initiates a real-time measurement of either the structure 114 or a distance between two different structures (not shown) similar to step 204 discussed above.

At 406, the operator manually positions a slice plane 420 to identify the proximal end 405 of the structure 114. Specifically, at 406, the operator manually positions the slice plane 420 at a first location 422 to measure either the non-linear structure 114 or a distance between two different structures (not shown). An exemplary 2D image 450 of the slice plane 460 at the first location 422 is shown in FIG. 8. In the exemplary embodiment, the operator may configure the imaging system 100 to operate in a slice mode. In the slice mode, the operator may observe the movement of the slice plane 420, in real-time, via the 2D image 450, as the slice plane 420 is being positioned or translated through the 3D volume dataset 110 to locate the proximal end 405 of the structure 114. In operation, the slice plane 420 is positioned by the operator until the slice plane 420 is at the first location 422 which represents a starting point in which the operator wishes to begin the measurement of either the structure 114 or a distance between two structures.

At 408, once the slice plane 420 is positioned at the first location 422, the operator clicks on the slice plane 420, via the user interface 120, to begin the measurement similar to step 208 discussed above. At 408 the measurement indication 254 is set to zero as shown in FIG. 4 and discussed above.

At 410, the operator manually moves or translates the slice plane 420 at least partially through the 3D volume dataset 110 until the slice plane 420 is at a different second location 430. The second location 430 may identify an intermediate point 432 between the proximal end 405 of the structure 114 and the distal end 407 of the structure 114. Optionally, the second location 430 may represent an intermediate point between two different structures. An exemplary 2D image 452 of the slice plane 420 at the second location 430 is shown in FIG. 8. In the exemplary embodiment, the slice plane 420 may positioned at a plurality of intermediate points. For example, in this exemplary embodiment, the slice plane 420 is positioned at the intermediate point 432 at the location 430 and an intermediate point 434 at a location 436 to generate a plurality of intermediate 2D images 452 and 454, respectively. An exemplary 2D image 454 of the slice plane 420 at the third location 436 is shown in FIG. 8. It should be realized that in the exemplary embodiment, that the operator translate the slice plane 420 until the slice plane 420 is at a desired intermediate position. The operator may then click on the slice plane 420 to generate the 2D image. Additionally, it should be realized that the measurement indication 254 continually updates as the slice plane 360 is being translated through the 3D volume dataset.

At 412, the operator positions the slice plane 420 at the distal end 407 of the structure 114 to end the measurement. An exemplary 2D image 458 of the slice plane 420 at the distal end 407 of the structure 114 is shown in FIG. 8. In operation, when the slice plane 420 is located at the proximal end 405 of the structure 114, the measurement indication 254 will indicate a measurement of approximately 0. When the slice plane 420 is located at the point 432 the measurement indication 254 will indicate a measurement of approximately $D_1$ which represents the distance between the proximal end 405 and the point 432. When the slice plane 420 is located at the point 434, the measurement indication 254 will indicate a measurement of approximately $D_2$ which represents a distance between the proximal end 405 and the point 434. When the slice plane 420 is located at the distal end 407, the measurement indication 254 will indicate a measurement of approximately $D_T$ which represents the total distance between the proximal end 405 and the distal end 407 of the structure 114. In another embodiment, the system 100 may include a plurality of measurement indications that may be used by the operator to view the distance between each point and the overall length of the structure 114.

At 414, the operator enters a command, via the user interface 120, to end the measurement. To enter the end measurement command, the operator may click on any location in the slice plane 420 when the slice plane 420 is located proximate to the distal end 407 of the structure 114. Optionally, the operator may click on a specific point in the slice plane 420.

At 416, the measurement indication 254 automatically provides a distance measurement that represents the distance between the proximal and distal ends 405 and 407 of the structure 114. Optionally, as discussed above, the measurement indication 254 may indicate a distance between various selected points on the structure 114.

Figure 9:
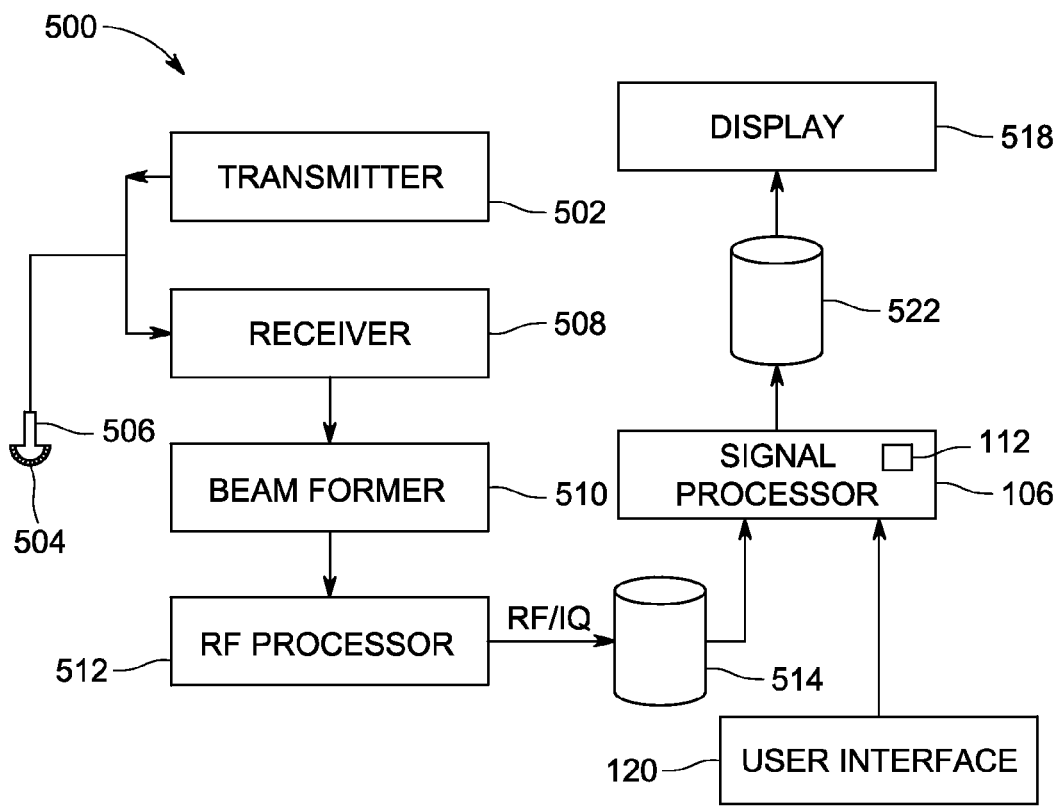
FIG. 9 illustrates a simplified block diagram of another ultrasound system formed in accordance with various embodiments.

The various embodiments described herein may be implemented on the imaging system shown in FIG. 9. Specifically, FIG. 9 illustrates a block diagram of an exemplary ultrasound system 500 that is formed in accordance with various embodiments. The ultrasound system 500 includes a transmitter 502 which drives a plurality of transducers 504 within an ultrasound probe 506 to emit pulsed ultrasonic signals into a body. A variety of geometries may be used. For example, the probe 506 may be used to acquire 2D, 3D, or 4D ultrasonic data, and may have further capabilities such as 3D beam steering. Other types of probes 506 may be used. The ultrasonic signals are back-scattered from structures in the body, like blood cells or muscular tissue, to produce echoes which return to the transducers 504. The echoes are received by a receiver 508. The received echoes are passed through a beamformer 510, which performs beamforming and outputs an RF signal. The beamformer may also process 2D, 3D and 4D ultrasonic data. The RF signal then passes through an RF processor 512. Alternatively, the RF processor 512 may include a complex demodulator (not shown) that demodulates the RF signal to form IQ data pairs representative of the echo signals. The RF or IQ signal data may then be routed directly to RF/IQ buffer 514 for temporary storage.

The ultrasound system 500 also includes a signal processor, such as signal processor 106 that includes the measurement module 112. The signal processor 106 processes the acquired ultrasound information (i.e., RF signal data or IQ data pairs) and prepare frames of ultrasound information for display on a display 518. The signal processor 106 is adapted to perform one or more processing operations according to a plurality of selectable ultrasound modalities on the acquired ultrasound information. Moreover, the measurement module 112 is configured to perform the various measurement embodiments described herein. Acquired ultrasound information may be processed in real-time during a scanning session as the echo signals are received. Additionally or alternatively, the ultrasound information may be stored temporarily in the RF/IQ buffer 514 during a scanning session and processed in less than real-time in a live or off-line operation. A user interface, such as user interface 120, allows an operator to enter data, enter and change scanning parameters, access protocols, measure structures of interest, and the like. The user interface 110 may be a rotating knob, switch, keyboard keys, mouse, touch screen, light pen, or any other suitable interface device. The user interface 120 also enables the operator to reposition or translate the slice planes used to perform measurements as described above.

The ultrasound system 500 may continuously acquire ultrasound information at a frame rate that exceeds 50 frames per second—the approximate perception rate of the human eye. The acquired ultrasound information, which may be the 3D volume dataset 110, is displayed on the display 518. The ultrasound information may be displayed as B-mode images, M-mode, volumes of data (3D), volumes of data over time (4D), or other desired representation. An image buffer 522 is included for storing processed frames of acquired ultrasound information that are not scheduled to be displayed immediately. Preferably, the image buffer 522 is of sufficient capacity to store at least several seconds worth of frames of ultrasound information. The frames of ultrasound information are stored in a manner to facilitate retrieval thereof according to its order or time of acquisition. The image buffer 522 may comprise any known data storage medium.

A technical effect of at least one embodiment is using the ultrasound data to calculate a length, width, diameter, etc. of a single structure or of determining a distance between two different structures. The various embodiments described herein facilitate enabling an operator to define different planes within an imaging volume that best illustrate the proximal and distal ends of a ROI. The distance between the various planes can then be calculated to determine the overall length of the ROI, or optionally, a distance between two different structures. As a result, various embodiments enable an operator to measure distances across two different 2D images at different locations in the 3D volume, in order to measure the distance between two different features that are difficult to visualize in a single 2D slice image.

While the invention has been described in terms of various specific embodiments, those skilled in the art will recognize that the invention can be practiced with modification within the spirit and scope of the claims.

Exemplary embodiments of an ultrasound system are described above in detail. The ultrasound system components illustrated are not limited to the specific embodiments described herein, but rather, components of each ultrasound system may be utilized independently and separately from other components described herein. For example, the ultrasound system components described above may also be used in combination with other imaging systems.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for measuring dimensions in volumetric ultrasound data, said system comprising:
   positioning, in real-time, a slice plane through the volumetric ultrasound dataset at a first location;
   repositioning the slice plane to a different second location;
   continually measuring a distance between the slice plane and the first location as the slice plane is being translated through the volumetric ultrasound data from the first location to the second location; and
   displaying the measured distance, wherein the measured distance updates as the slice plane is translated.

2. The method of claim 1, further comprising:
   receiving an operator input identifying a first and a second position on the slice plane; and
   displaying the distance between the first and second positions on the display.

3. The method of claim 1, further comprising repositioning the slice plane to a different second location that is parallel to the first location.

4. The method of claim 3, further comprising displaying the distance, in real-time, as the slice plane is repositioned from the first location to the second location.

5. The method of claim 3, further comprising displaying the distance based on a second operator input indicating that the slice plane is at the second different location.

6. The method of claim 3, further comprising:
displaying a first image plane when the slice plane is at the first location;
displaying a second image plane, concurrently with the first image plane, when the slice plane is at the second location;
enabling an operator to reposition either the first or second image planes based on an operator input; and
displaying a distance between the first and second image planes.

7. The method of claim 2, further comprising repositioning the slice plane to a different second location that is non-parallel to the first location.

8. The method of claim 7, further comprising:
displaying a first image plane when the slice plane is at the first location;
displaying a second image plane, concurrently with the first image plane, when the slice plane is at the second location;
enabling an operator to reposition either the first or second image planes based on an operator input; and
displaying a distance between the first and second image planes.

9. A system for measuring dimensions in volumetric ultrasound data, said system comprising:
a display for displaying a volumetric ultrasound dataset;
a user interface enabling an operator to position, in real-time a slice plane through the volumetric ultrasound dataset at a first location and reposition the slice plane to a different second location;
a processor continually measuring a distance between the slice plane and the first location as the slice plane is being translated through the volumetric ultrasound data from the first location to the second location; and
a display displaying the measured distance, wherein the measured distance updates as the slice plane is translated.

10. The system of claim 9 wherein the user interface is further configured to enable an operator to identify a first and a second position on the slice plane, the display is further configured to display the distance between the first and second positions.

11. The system of claim 9, wherein the user interface is further configured to enable a operator to position, in real-time a slice plane through the volumetric ultrasound dataset at a first location, receive an operator input to begin a measurement, and enable the operator to reposition the slice plane to a different second location that is parallel to the first location.

12. The system of claim 10, wherein in the display is further configured to display the distance, in real-time, as the slice plane is repositioned from the first location to the second location.

13. The system of claim 10, wherein the user interface is further configured to enable the operator enter an input indicating that the slice plane is at the second different location, the display is further configured to display the distance based on the operator input.

14. The system of claim 10, wherein the display is configured to display a first image plane when the slice plane is at the first location, and display a second image plane, concurrently with the first image plane, when the slice plane is at the second location, the user interface enabling the operator to reposition either the first or second image planes based on an operator input.

15. The system of claim 10, wherein the user interface is further configured to enable a operator to position, in real-time a slice plane through the volumetric ultrasound dataset at a first location, receive an operator input to begin a measurement, and enable the operator to reposition the slice plane to a different second location that is non-parallel to the first location.

16. The system of claim 15, wherein the display is configured to display a first image plane when the slice plane is at the first location, and display a second image plane, concurrently with the first image plane, when the slice plane is at the second location, the user interface enabling the operator to reposition either the first or second image planes based on an operator input.

17. A non-transitory computer readable medium for measuring dimensions in volumetric ultrasound data, said non-transitory computer readable medium programmed to:
receive an operator input to position, in real-time a slice plane through the volumetric ultrasound dataset at a first location;
receive an operator input to reposition the slice plane to a different second location;
continually measure a distance between the slice plane at the first and second locations as the slice plane is being translated; and
display a numeric indication of the measured distance between the slice plane at the first and second locations on a display.

18. The non-transitory computer readable medium of claim 17, wherein the computer readable medium is further programmed to:
receive an operator input identifying a first and a second position on the slice plane; and
display the distance between the first and second positions on the display.

19. The non-transitory computer readable medium of claim 17, wherein the computer readable medium is further programmed to reposition the slice plane to a different second location that is parallel to the first location.

20. The non-transitory computer readable medium of claim 17, wherein the computer readable medium is further programmed to reposition the slice plane to a different second location that is non-parallel to the first location.

* * * * *